US008124710B2

(12) United States Patent
Cook et al.

(10) Patent No.: US 8,124,710 B2
(45) Date of Patent: Feb. 28, 2012

(54) MQ-T PROPYL SILOXANE RESINS

(75) Inventors: Julie Lyn Cook, Turner, MI (US);
Daniel Michael Hinterman, Midland, MI (US); Lori Ann Stark-Kasley, Midland, MI (US); Gary Michael Wieber, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 972 days.

(21) Appl. No.: 10/585,837

(22) PCT Filed: Jan. 20, 2005

(86) PCT No.: PCT/US2005/002451
§ 371 (c)(1),
(2), (4) Date: Jul. 12, 2006

(87) PCT Pub. No.: WO2005/075542
PCT Pub. Date: Aug. 18, 2005

(65) Prior Publication Data
US 2007/0148115 A1 Jun. 28, 2007

Related U.S. Application Data

(60) Provisional application No. 60/541,002, filed on Feb. 2, 2004.

(51) Int. Cl.
*C08G 77/06* (2006.01)
(52) U.S. Cl. .............. 528/10; 528/14; 528/39
(58) Field of Classification Search ............ None
See application file for complete search history.

(56) References Cited

U.S. PATENT DOCUMENTS

| | | | |
|---|---|---|---|
| 2,814,601 A | 11/1957 | Currie et al. | |
| 2,857,356 A | 10/1958 | Goodwin | |
| 5,063,254 A | 11/1991 | Nakos | |
| 5,075,103 A | 12/1991 | Halloran et al. | |
| 5,085,859 A | 2/1992 | Halloran et al. | |
| 5,110,890 A * | 5/1992 | Butler | 528/12 |
| 5,330,747 A | 7/1994 | Krzysik | |
| 5,733,537 A | 3/1998 | Halloran et al. | |
| 5,837,223 A | 11/1998 | Barone et al. | |
| 5,837,784 A | 11/1998 | Vincent | |
| 6,036,947 A | 3/2000 | Barone et al. | |
| 6,071,503 A | 6/2000 | Drechsler et al. | |
| 6,074,654 A | 6/2000 | Drechsler et al. | |
| 6,139,823 A | 10/2000 | Drechsler et al. | |
| 6,340,466 B1 | 1/2002 | Drechsler et al. | |
| 6,406,683 B1 | 6/2002 | Drechsler et al. | |
| 6,825,264 B2 * | 11/2004 | Oda et al. | 524/537 |
| 2002/0031488 A1 | 3/2002 | Kanji et al. | |
| 2002/0058054 A1 | 5/2002 | Arnaud | |
| 2002/0114773 A1 | 8/2002 | Kanji et al. | |
| 2002/0187170 A1 | 12/2002 | Pavlin | |
| 2003/0236387 A1 | 12/2003 | Pavlin | |
| 2004/0180011 A1 | 9/2004 | Schlosser | |

FOREIGN PATENT DOCUMENTS

| | | |
|---|---|---|
| EP | 0 336 633 | 10/1989 |
| GB | 2 294 392 | 5/1996 |
| GB | 2 319 527 | 5/1998 |
| JP | 61158910 | 7/1986 |
| JP | 4139114 | 5/1992 |
| JP | 1994-72085 | 9/1994 |
| JP | 7330536 | 12/1995 |
| KR | 2002054603 | 7/2002 |
| WO | WO 97/17058 | 5/1997 |
| WO | WO 97/17059 | 5/1997 |
| WO | WO 02/089760 | 11/2002 |
| WO | WO 2005/075567 | 8/2005 |

* cited by examiner

*Primary Examiner* — Marc Zimmer
(74) *Attorney, Agent, or Firm* — Patricia M. Scaduto

(57) ABSTRACT

MQ-T propyl siloxane resins comprising $(R^1_3SiO_{1/2})_a$, $(R^2_2SiO_{2/2})_b$, $(R^3SiO_{3/2})_c$, and $(SiO_{4/2})_d$ units, where at least 40 mole % of the $R^3$ groups are propyl are disclosed. A method of preparing such siloxane resins by reacting a MQ siloxane resin with a T propyl siloxane resin is also disclosed. These siloxane resins are useful in a variety of personal, household, and medical care applications, and in particular, as a resin additive in pigmented cosmetic formulations.

9 Claims, No Drawings

MQ-T PROPYL SILOXANE RESINS

CROSS REFERENCE TO RELATED APPLICATIONS

This application is a U.S. national stage filing under 35 U.S.C. §371 of PCT Application No. PCT/US05/002451 filed on 20 Jan. 2005, currently pending, which claims the benefit of U.S. Provisional Patent Application No. 60/541,002 filed 2 Feb. 2004 under 35 U.S.C. §119 (e). PCT Application No. PCT/US05/002451 and U.S. Provisional Patent Application No. 60/541,002 are hereby incorporated by reference.

FIELD OF THE INVENTION

The present invention provides siloxane resins, herein known as MQ-T propyl resins, comprising $(R^1{}_3SiO_{1/2})_a$, $(R^2{}_2SiO_{2/2})_b$, $(R^3SiO_{3/2})_c$, and $(SiO_{4/2})_d$ units, where at least 40 mole % of the $R^3$ groups are propyl. The present invention further relates to a method of preparing such siloxane resins by reacting a MQ siloxane resin with a T propyl siloxane resin. The siloxane resins of the present invention are useful in a variety of personal, household, automotive, and medical care applications, and in particular, as a resin additive in pigmented cosmetic formulations.

BACKGROUND OF THE INVENTION

Siloxane resins of the general formula $R_nSiO_{(4-n)/2}$, where R is an alkyl group and n is generally less than 1.8, are an important family of silicone polymers because of their utility in many commercial applications such as adhesive compositions and coatings applications. One particular subclass of siloxane resins, known as MQ resins (since they comprise primarily of "M" units of the general formula $R_3SiO_{1/2}$ and "Q" units of the general formula $SiO_2$), have found utility in cosmetic formulations. In particular, MQ resins are commonly used in "extended wear" or "transfer resistant" cosmetic formulations. In these formulations, MQ resins enhance the substantivity of the pigments or other formulation actives to skin after application creating a longer lasting, and hence extended wear product.

Representative examples of transfer resistant cosmetic compositions using MQ resins are found in U.S. Pat. No. 6,071,503, U.S. Pat. No. 6,074,654, U.S. Pat. No. 6,139,823, U.S. Pat. No. 6,340,466, WO 97/17058, and WO 97/17059 which disclose compositions comprising the combination of organosiloxane resins and fluid diorganosiloxane resins with a volatile carrier.

U.S. Pat. No. 5,330,747 teaches cosmetics with enhanced durability using a film forming agent from a pressure sensitive adhesive composition comprising a trimethylsilyl endblocked resinous copolymer, a silanol endblocked polydiorganosiloxane fluid, and a phenyl containing polysiloxane fluid.

U.S. Pat. No. 5,075,103 and U.S. Pat. No. 5,733,537 teach a hair treating method for imparting curl retention to hair in which at least one film forming ingredient is applied to the hair. The improvement utilizes as the film forming ingredient an organosilicon compound which is a nonpolar silsesquioxane.

U.S. Pat. No. 5,800,816 discloses cosmetic compositions having improved transfer resistance comprising: a) from about 0.1-60% by weight of trimethylated silica, b) from about 0.1-60% by weight of a volatile solvent having a viscosity of 0.5 to 100 centipoise (mPa·s) at 25° C., c) 0.1-60% by weight of a nonvolatile oil having a viscosity of 200 to 1,000,000 centipoise (mPa·s) at 25° C., d) 0.1-80% of a cosmetically acceptable carrier.

U.S. Pat. No. 5,837,223 and U.S. Pat. No. 6,036,947 teach transfer resistant high luster cosmetic stick compositions comprising, by weight of the total composition: a) 10-70% of a volatile solvent having a viscosity of 0.5 to 20 centipoise (mPa·s) at 25.degree. C., b) 0.5-40% of a guerbet ester, and c) 0.1-20% of a siloxysilicate polymer.

GB 2,319,527 discloses fragrance releasing non-volatile polysiloxanes based on a high molecular weight polydiorganosiloxane compounds where at least one or more of the organic substituents of the polymer is a radical derived from a fragrant alcohol.

Japanese examined patent publication 1994-72085 teaches makeup cosmetic compositions having improved water resistance and durability containing an organic silicone resin, a volatile silicone oil, and a make up powder.

While the use of MQ resins in cosmetics have led to formulations having extended wear or transfer resistance, a need exists to alter the properties of the siloxane resins used in such formulations. In particular, films of MQ resins used in these formulations can have a matte finish and feel tacky. Thus, there is a need for improved siloxane resins that offer at least comparable extended wear and transfer resistance properties of the MQ resins presently used in cosmetic formulations, but having improved gloss (i.e. non-matte) that are non-tacky. Furthermore, there is a need for resins in hair care formulations that improve the curl retention properties of hair following treatment.

The present inventors have discovered improved siloxane resins by incorporating propyl containing siloxane $(R^3SiO_{3/2})_c$ units (T units) with M and Q units. The resulting siloxane resins, herein referred to as MQ-T propyl siloxane resins, have improved physical properties. In particular, cosmetic formulations containing the present MQ-T propyl siloxane resins have improved gloss vs MQ resins and are less tacky than T propyl resins, while maintaining their long lasting or wear characteristics.

SUMMARY OF THE INVENTION

This invention relates to a MQ-T propyl siloxane resin comprising the units:
(i) $(R^1{}_3SiO_{1/2})_a$
(ii) $(R^2{}_2SiO_{2/2})_b$
(iii) $(R^3SiO_{3/2})_c$, and
(iv) $(SiO_{4/2})_d$
wherein
$R^1$, $R^2$, and $R^3$ are independently an alkyl group having from 1 to 8 carbon atoms, an aryl group, a carbinol group, or an amino group,
a has a value 0.05 to 0.5,
b has a value of zero to 0.3, c has a value greater than zero,
d has a value of 0.05 to 0.6,
the value of a+b+c+d=1,
with the proviso that greater than 40 mole % of the $R^3$ groups in the siloxane resin are propyl.

The invention further relates to a method of making a siloxane resin composition and the products obtained therefrom. The method comprises reacting:

A) a MQ resin comprising at least 80 mole % $(R^1{}_3SiO_{1/2})_a$ and $(SiO_{4/2})_d$ units
where $R^1$ is an alkyl group having from 1 to 8 carbon atoms, an aryl group,
a carbinol group, or an amino group,
a and d has a value greater than zero,
the ratio of a/d is 0.5 to 1.5;
and B) a T propyl resin comprising at least 80 mole % $R^3SiO$ units,
where $R^3$ is an alkyl group having from 1 to 8 carbon atoms, an aryl group,
a carbinol group, or an amino group,
c has a value greater than zero,
and with the provisio that at least 40 mole % of the $R^3$ groups are propyl, wherein the weight ratio of A/B is from 95:5 to 15:85.

The MQ-T propyl siloxane resins are useful in a variety of personal, household, or medical care compositions. In particular, the MQ-T propyl siloxane resins provide glossy, non-tacky films that can be used to enhance the substantivity of color cosmetic formulations. The MQ-T propyl siloxane resins can also be used as additives in hair care formulations to enhance curl retention properties. The MQ-T propyl siloxane resins can also enhance the feel of treated hair, providing a softer feel compared to other siloxane resin additives. Thus, the present invention provides personal, household, or medical care compositions comprising the MQ-T propyl siloxane resins described herein.

DETAILED DESCRIPTION OF THE INVENTION

The MQ-T propyl siloxane resin of the present invention comprises (i) $R^1{}_3SiO_{1/2})_a$, (ii) $(R^2{}_2SiO_{2/2})_b$, (iii) $(R^3SiO_{3/2})_c$, and (iv) $(SiO_{4/2})_d$ units which are commonly known in the art, and also used herein, as M, D, T, and Q units respectively. The amount of each unit present in the MQ-T propyl siloxane resin can be expressed as a mole fraction (i.e. a, b, c, or d) of the total number of moles of all M, D, T, and Q units present in the MQ-T propyl siloxane resin. The value of a (mole fraction of M units) is 0.05-0.5, or alternatively 0.15 to 0.4. The value of b (mole fraction of D units) is 0-0.3, alternatively 0 to 0.1, or alternatively 0 to 0.05. Thus, the MQ-T propyl siloxane resins can be free of D units, or alternatively can contain up to and including 0.3 mole fraction of D units. The value of c (mole fraction of T units) is greater than 0, alternatively 0.05 to 0.65, or alternatively 0.4 to 0.65. The value of d (mole fraction of Q units) is 0.05 to 0.6, alternatively 0.2 to 0.6, or alternatively 0.2 to 0.55.

The MQ-T propyl siloxane resins of the present invention are characterized by having at least 40 mole %, alternatively 50 mole %, or alternatively 90 mole % of the $R^3$ alkyl groups on the T unit be propyl.

The $R^1$, $R^2$, and $R^3$ in the units of the MQ-T propyl siloxane resin are independently an alkyl group having from 1 to 8 carbon atoms, an aryl group, a carbinol group, or an amino group. The alkyl groups are illustrated by methyl, ethyl, propyl, butyl, pentyl, hexyl, and octyl. The aryl groups are illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl with the aryl group typically being phenyl.

For the purposes of this invention a "carbinol group" is defined as any group containing at least one carbon-bonded hydroxyl (COH) radical. Thus the carbinol groups may contain more than one COH radical such as for example

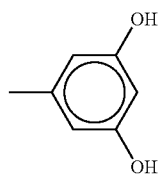

The carbinol group if free of aryl groups has at least 3 carbon atoms, or an aryl-containing carbinol group having at least 6 carbon atoms, The carbinol group free of aryl groups having at least 3 carbon atoms is illustrated by groups having the formula $R^4OH$ wherein $R^4$ is a divalent hydrocarbon radical having at least 3 carbon atoms or divalent hydrocarbonoxy radical having at least 3 carbon atoms. The group $R^4$ is illustrated by alkylene radicals such as —$(CH_2)_x$— where x has a value of 3 to 10, —$CH_2CH(CH_3)$—, —$CH_2CH(CH_3)CH_2$—, —$CH_2CH_2CH(CH_2CH_3)CH_2CH_2CH_2$—, and —$OCH(CH_3)(CH_2)_x$— wherein x has a value of 1 to 10.

The aryl-containing carbinol group having at least 6 carbon atoms is illustrated by groups having the formula $R^5OH$ wherein $R^5$ is an arylene radical such as —$(CH_2)_xC_6H_4$— wherein x has a value of 0 to 10, —$CH_2CH(CH_3)(CH_2)_xC_6H_4$— wherein x has a value of 0 to 10, —$(CH_2)_xC_6H_4(CH_2)_x$— wherein x has a value of 1 to 10. The aryl-containing carbinol groups typically have from 6 to 14 atoms.

The amino group is illustrated by groups having the formula —$R^6NH_2$ or —$R^6NHR^7NH_2$ wherein $R^6$ is a divalent hydrocarbon radical having at least 2 carbon atoms and $R^7$ is a divalent hydrocarbon radical having at least 2 carbon atoms. The group $R^6$ is typically an alkylene radical having from 2 to 20 carbon atoms. $R^6$ is illustrated by ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

$R^7$ is typically an alkylene radical having from 2 to 20 carbon atoms. $R^7$ is illustrated by ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

Typical amino groups are —$CH_2CH_2CH_2NH_2$ and —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$, and —$CH_2CH_2NHCH_2CH_2NHC_4H_9$.

Typically, $R^1$ is a methyl group, $R^2$ is a methyl or phenyl group, and $R^3$ is a propyl group.

Any individual D, T or Q siloxane units of the MQ-T propyl siloxane resins can also contain a hydroxy group and/or alkoxy group. Such siloxane units containing hydroxy and/or alkoxy groups are commonly found in siloxane resins having the general formula $R_nSiO_{(4-n)/2}$. The hydroxy groups in these siloxane resins typically result from the reaction of the hydrolyzable group on the siloxane unit with water; the alkoxy groups result from incomplete hydrolysis when alkoxysilane precursors are used or from exchange of alcohol with hydrolysable groups. Typically, the weight percent of the total hydroxy groups present in the MQ-T propyl siloxane resin is 3%, alternatively, 2%, or alternatively, 1.5%. Typically, the weight percent of the total alkoxy groups present in the MQ-T propyl siloxane resin is up to 20%, alternatively up to 10%.

The molecular weights of the MQ-T propyl siloxane resins are not restricted, but typically the number average molecular weight ($M_N$) ranges from 3,000 to 10,000, or alternatively from 5,000 to 8,000.

The MQ-T propyl siloxane resins of the present invention can be prepared by any of the methods known in the art for preparing siloxane resins having the general formula $R_nSiO_{(4-n)/2}$ where R is an alkyl group and n is generally less than 1.8. Alternatively, the MQ-T propyl resins can be prepared by the methods described infra.

The MQ-T propyl resins of this invention are illustrated by:

MQ-T propyl resins comprising the units;
$((CH_3)_3SiO_{1/2})_a$,
$(R^3SiO_{3/2})_c$, where $R^3$=$CH_3CH_2CH_2$—, and
$(SiO_{4/2})_d$ MQ-T propyl resins comprising the units;
$((CH_3)_3SiO_{1/2})_a$,
$((CH_3)_2SiO_{2/2})_b$,
$(R^3SiO_{3/2})_c$, where $R^3$=$CH_3CH_2CH_2$—, and
$(SiO_{4/2})_d$ MQ-T propyl resins comprising the units;
$((CH_3)_3SiO_{1/2})_a$,
$((CH_3)_2SiO_{2/2})_b$, $((CH_3)(C_6H_5)SiO_{2/2})_{b'}$,
$(R^3SiO_{3/2})_c$, where $R^3$=$CH_3CH_2CH_2$—, and
$(SiO_{4/2})_d$ MQ-T propyl resins comprising the units;
$((CH_3)_3SiO_{1/2})_a$,
$((CH_3)_2SiO_{2/2})_b$,
$(R^3SiO_{3/2})_c$, where $R^3$=$CH_3CH_2CH_2$—, and $(C_6H_5SiO_{3/2})_c$
$(SiO_{4/2})_d$ MQ-T propyl resins comprising the units;
$((CH_3)_3SiO_{1/2})_a$,
$((CH_3)_2SiO_{2/2})_b$, $((CH_3)(C_6H_5)SiO_{2/2})_{b'}$,
$(R^3SiO_{3/2})_c$, where $R^3$=$CH_3CH_2CH_2$—, $(C_6H_5SiO_{3/2})_c$, and
$(SiO_{4/2})_d$ wherein a has a total value in the resin of 0.05 to 0.5, the sum of b+b' has a total value in the resin of zero to 0.3, c has a total value in the resin of 0.05 to 0.65, and d has a total value in the resin of 0.05 to 0.6.

The present invention also provides a method of making a siloxane resin composition and the products obtained therefrom. The method comprises reacting:

A) a MQ resin comprising at least 80 mole % $(R^1_3SiO_{1/2})_a$ and $(SiO_{4/2})_d$ units
where $R^1$ is an alkyl group having from 1 to 8 carbon atoms, an aryl group,
a carbinol group, or an amino group,
a and d has a value greater than zero,
the ratio of a/d is 0.5 to 1.5;
and B) a T propyl resin comprising at least 80 mole % $R^3SiO$ units,
where $R^3$ is an alkyl group having from 1 to 8 carbon atoms, an aryl group,
a carbinol group, or an amino group,
c has a value greater than zero,
and with the provisio that at least 40 mole % of the $R^3$ groups are propyl, wherein the weight ratio of A/B is from 95:5 to 15:85.

Component A) is a MQ resin comprising at least 80 mole % $R^1_3SiO_{1/2})_a$ and $(SiO_{4/2})_d$ units where $R^1$ is the same as defined above, i.e. an alkyl group having from 1 to 8 carbon atoms an aryl group, a carbinol group, or an amino group, a and d has a value greater than zero, and the ratio of a/d is 0.5 to 1.5. MQ resins suitable for use as component (A), and methods for their preparation, are known in the art. For example, U.S. Pat. No. 2,814,601 to Currie et al., Nov. 26, 1957, which is hereby incorporated by reference, discloses that MQ resins can be prepared by converting a water-soluble silicate into a silicic acid monomer or silicic acid oligomer using an acid. When adequate polymerization has been achieved, the resin is end-capped with trimethylchlorosilane to yield the MQ resin. Another method for preparing MQ resins is disclosed in U.S. Pat. No. 2,857,356 to Goodwin, Oct. 21, 1958, which is hereby incorporated by reference. Goodwin discloses a method for the preparation of an MQ resin by the cohydrolysis of a mixture of an alkyl silicate and a hydrolyzable trialkylsilane organopolysiloxane with water.

The MQ resins suitable as component A) in the present invention may contain D and T units, providing that at least 80 mole %, alternatively 90 mole % of the total siloxane units are M and Q units. The MQ resins may also contain hydroxy groups. Typically, the MQ resins have a total weight % hydroxy content of 2-10 weight %, alternatively 2-5 weight %. The MQ resins can also be further "capped" wherein residual hydroxy groups are reacted further with M groups.

Component B) is a T propyl resin comprising at least 80 mole % of $R^3SiO_{3/2}$ units, where $R^3$ is the same as defined above, i.e. an alkyl group having from 1 to 8 carbon atoms an aryl group, a carbinol group, or an amino group, and with the proviso that at least 40 mole % of the $R^3$ groups are propyl. Typically, the T propyl resin is a silsesquioxane resin. Silsesquioxane resins are well known in the art and are typically prepared by hydrolyzing an organosilane having three hydrolyzable groups, such as a halogen or alkoxy group, present in the molecule. Thus, component (B) can be obtained by hydrolyzing propyltrimethoxysilane, propyltriethoxysilane, propyltripropoxysilane, or by co-hydrolyzing the aforementioned propylalkoxysilanes with various alkoxysilanes. Examples of these alkoxysilanes include methyltrimethoxysilane, methyltriethoxysilane, methyltriisopropoxysilane, dimethyldimethoxysilane, and phenyltrimethoxysilane. Propyltrichlorosilane can also be hydrolyzed alone, or in the presence of alcohol. In this case, co-hydrolyzation can be carried out by adding methyltrichlorosilane, dimethyldichlorosilane, phenyltrichlorosilane, or similar chlorosilanes and methyltrimethoxysilane, methyltriethoxysilane, methyltriisopropoxysilane, or similar methylalkoxysilane. Alcohols suitable for these purposes include methanol, ethanol, n-propyl alcohol, isopropyl alcohol, butanol, methoxy ethanol, ethoxy ethanol, or similar alcohols. Examples of hydrocarbon-type solvents which can also be concurrently used include toluene, xylene, or similar aromatic hydrocarbons; hexane, heptane, isooctane, or similar linear or partially branched saturated hydrocarbons; and cyclohexane, or similar aliphatic hydrocarbons.

The T-propyl resins suitable as component B) in the present invention may contain M, D, and Q units, providing that at least 80 mole %, alternatively 90 mole % of the total siloxane units are T units. The T-propyl resins may also contain hydroxy groups. Typically, the T-propyl resins have a total weight % hydroxy content of 3-8 weight %.

A polyorganosiloxane can optionally be added to the method of the present invention as component C). Polyorganosiloxane useful as component C) in the present invention comprise $R^2_2SiO_{2/2}$, (i.e. D units) or $R^3SiO_{3/2}$ (T units). The polyorganosiloxane can be added to introduce various D and T units into MQ-T propyl resins to alter the properties of the resulting resins. The structure or formula of the polyorganosiloxane is not restrictive, providing the polyorganosiloxane contains some measurable quantity of $R^2_2SiO_{2/2}$, units (i.e. D units) or $R^3SiO_{3/2}$ (T units), and the total amount of polyorganosiloxane added to the reaction of A) and B) does not provide more than 50 mole % D or T units into the reaction mixture. The polyorganosiloxane can contain any combination of M, D, T and Q units, providing at least some D or T units are present. Thus, the polyorganosiloxane can be selected from any of the fluid, gum, or resinous silicones known in the art containing D or T units, or combinations thereof. The D units typically contain methyl or phenyl as the $R^2$ substituents, which can be designated as $D^{Me}$ and $D^{Ph}$ respectively, or any combinations thereof. The T units typically contain methyl or phenyl as the $R^3$ substituents, which can be designated as $T^{Me}$ and $T^{Ph}$ respectively, or any combinations thereof. The polyorganosiloxane can be a linear polydiorganosiloxane fluid having a viscosity of 10-1000 cS (mm$^2$/s). Typically the polydiorganosiloxane fluid is polydimethylsiloxane, or alternatively a polymethylphenylsiloxane. The polyorganosiloxane can also be an organosilsequioxane resin. The organosilsequioxane resin typically is a methylsilsesquioxane resin or a phenylsilsequixone resin.

Components A), B), and optionally C) can be reacted by any method in the art known to effect reaction of M, D, T, and Q siloxane units. Typically however, components A), B), and optionally C) are reacted by a condensation reaction in the presence of a catalyst. Typically the MQ resin is contained in an aromatic hydrocarbon or siloxane solvent. Suitable condensation reaction catalysts are base catalysts including metal hydroxides such as potassium hydroxide and sodium hydroxide; metal salts such as silanolates, carboxylates, and carbonates; ammonia; amines; and titanates such as tetrabutyl titanates; and combinations thereof. Typically the reaction of components A), B), and optionally C) is effected by heating the reaction mixture to temperatures ranging from 50 to 140° C., alternatively 100 to 140° C. The reaction can be conducted in a batch, semi-continuous, or continuous process.

The weight ratio of component A) to component B) (i.e. A/B) in the reaction can vary from 95:5 to 15:85, alternatively 95:5 to 20:80, or alternatively 90:10 to 20:80. The amount of component C) can vary, but the amount of component C) added should introduce less than 30 mole % of additional D or T units, based on the total moles of siloxane units in the reaction mixture.

The MQ-T propyl resins of the present invention are useful in a variety of personal, household, automotive, or medical care applications. In particular, the MQ-T propyl siloxane resins provide glossy, non-tacky films that can be used to enhance the substantivity of color cosmetic formulations. The MQ-T propyl siloxane resins can also be used in hair care formulations to enhance curl retention properties. Thus, the present invention provides personal, household, automotive, or medical care compositions comprising the MQ-T propyl siloxane resins described herein.

EXAMPLES

The following examples are presented to further illustrate the compositions and methods of this invention, but are not to be construed as limiting the invention. All parts and percentages in the examples are on a weight basis and all measurements were obtained at about 23° C., unless indicated to the contrary.

Materials

MQ Resin=a MQ resin having the formula $M_{0.43}Q_{0.57}$ and $M_n$=3230 dissolved in xylene at 70.8 wt % solids. The MQ resin was prepared according to techniques taught by Daudt in U.S. Pat. No. 2,676,182.

T propyl resin=propyl silsesquioxane resin at 74.8 wt % in toluene. The propyl silsesquioxane resin was prepared from the hydrolysis of propyl trichlorosilane.

Phenyl silsesquioxane resin=a phenyl silsesquioxane solid flake resin at 100 wt % solids prepared from the hydrolysis of phenyl trichlorosilane.

Example 1

Preparation of MQT$^{Pr}$ Resins

A 3-neck reaction flask equipped with an agitator, temperature probe, and a Dean Stark trap fitted with a condenser on top, was loaded with MQ Resin, T propyl resin, xylene and 1M KOH in water at the ratios as shown in Table 1. The Dean Stark trap was pre-loaded with xylene to insure a 50% solids level in the reaction flask was maintained. The mixture in the flask was maintained at reflux temperature (100-140° C.) for at least 3 hours. Any water that formed in the reaction mixture was continuously removed as needed and trapped as an azeotrope in the Dean Stark trap. After 3 hours of reflux, water was removed from the trap, and heating continued for an additional 30 min. After allowing the mixture to cool, excess acetic acid was added to neutralize the KOH in the mixture. The mixture was then filtered to remove the salts formed by passing it through a pressure filter. A solvent exchange was completed by heating the mixture in a rotary evaporator under vacuum. After the majority of xylene was removed, decamethylcyclopentasiloxane was added while continuing to remove any residual aromatic solvent. The structures of the resulting siloxane resins were characterized by $^{29}$Si NMR spectroscopy and GPC and the results summarized in Table 4 below.

TABLE 1

| Example # | Wt Ratio MQ/$T^{Pr}$ resins added | Wt % MQ Resin | Wt % T Propyl Resin | Wt % Xylene | Wt % 1M KOH | Wt % Acetic Acid |
|---|---|---|---|---|---|---|
| 1-a | (85:15) | 59.4 | 10.5 | 29.1 | 0.9 | 0.2 |
| 1-b | (50:50) | 34.9 | 34.8 | 29.1 | 0.9 | 0.2 |
| 1-c | (30:70) | 20.9 | 48.8 | 29.2 | 0.9 | 0.2 |
| 1-d | (95:5) | 67.1 | 3.5 | 28.3 | 0.9 | 0.2 |
| 1-e | (100:0) | 69.3 | 0 | 28.8 | 0.9 | 0.2 |

Example 2

Preparation of $MQT^{Pr}T^{Ph}$ Resins

A series of $MQT^{Pr}T^{Ph}$ resins were prepared following the experimental procedure described in Example 1 using the formulations shown in Table 2. In this series, a phenyl silsesquioxane resin was added to incorporate additional phenyl containing T units into the siloxane resin. The structures of the resulting siloxane resins were characterized by $^{29}$Si NMR spectroscopy and GPC, as summarized in Table 4 below.

TABLE 2

| Example # | Wt Ratio MQ/$T^{Pr}$/$T^{Ph}$ resins | Wt % MQ Resin | Wt % T Propyl Resin | Wt % T Phenyl Resin | Wt % of Xylene | Wt of 1M KOH solution in water | Wt of Glacial Acetic Acid |
|---|---|---|---|---|---|---|---|
| 2-a | (85:7.5:7.5) | 59.4 | 5.2 | 3.7 | 30.6 | 0.9 | 0.2 |
| 2-b | (50:25:25) | 34.7 | 17.4 | 12.4 | 34.4 | 0.9 | 0.2 |
| 2-c | (15:42.5:42.5) | 10.5 | 29.6 | 21.0 | 37.8 | 0.9 | 0.2 |

Example 3

Preparation of $MQT^{Pr}D$ Resins

Two $MQT^{Pr}D$ resins were prepared following the experimental procedure described in Example 1 using the formulations shown in Table 3. In this series, a 100 cst polydimethylsiloxane fluid was added to incorporate D units ($Me_2SiO$) into the siloxane resin. The structures of the resulting siloxane resins were characterized by $^{29}$Si NMR spectroscopy and GPC, as summarized in Table 4 below.

TABLE 3

| Example # | Wt Ratio MQ/$T^{Pr}$/D added | Wt % MQ Resin | Wt % T Propyl Resin | Wt % D | Wt % of Xylene | Wt of 1M KOH solution in water | Wt of Glacial Acetic Acid |
|---|---|---|---|---|---|---|---|
| 3-a | (38:57:5) | 26.9 | 39.7 | 2.5 | 29.9 | 0.9 | 0.2 |
| 3-b | (28.5:66.5:5) | 14.1 | 32.9 | 2.5 | 30.0 | 0.9 | 0.2 |

TABLE 4

| Example # | Resin structure according to NMR Characterization | wt % OH | Mn | Mw | Mw/Mn |
|---|---|---|---|---|---|
| MQ resin | $M^{0.43}Q^{0.57}$ | | 3230 | 1516 | 4.7 |
| T propyl resin | $T^{Pr}_{1.0}$ | 7.0 | 3470 | 11400 | 3.3 |
| 1-a | $M_{0.374}Q_{0.529}$:$T^{Pr}_{0.097}$ | 1.4 | 5880 | 271000 | 46.1 |
| 1-b | $M_{0.248}Q_{0.341}$:$T^{Pr}_{0.412}$ | 2.1 | 6640 | 3860000 | 581.3 |
| 1-c | $M_{0.162}Q_{0.217}$:$T^{Pr}_{0.621}$ | 1.5 | 7600 | 25300000 | 3329 |
| 1-d | $M_{0.419}Q_{0.5485}$:$T^{Pr}_{0.03}$ | 1.5 | | | |
| 1-e | M Q | 1.7 | 5200 | 28900 | 5.6 |
| 2-a | $M_{0.396}Q_{0.523}$:$T^{Pr}_{0.0491}$:$T^{Ph}_{0.0339}$ | 1.6 | 5200 | 26900 | 5.2 |
| 2-b | $M_{0.272}Q_{0.347}$:$T^{Pr}_{0.220}$:$T^{Ph}_{0.161}$ | 0.8 | 5867 | 1640000 | 279 |
| 2-c | $M_{0.09}Q_{0.118}$:$T^{Pr}_{0.457}$:$T^{Ph}_{0.334}$ | 0.8 | | | |
| 3-a | MQ:$T^{Pr}$:$D^{Me2}$ | | 5455 | 303000 | 55.5 |
| 3-b | $M_{0.155}Q_{0.201}$:$T^{Pr}_{0.591}$:$D^{Me2}_{0.053}$ | 1.8 | 5140 | 295000 | 57.4 |

Films resulting from the siloxane resins of Examples 1-3 were evaluated for gloss and tack after coating from 35% solids in volatile solvent onto a Leneta chart, evaluated in a foundation (color cosmetic) for durability, and in a hair fixative for curl retention and conditioning. The results are summarized in Table 6. The siloxane resins were applied to the hair tresses as 6 wt. % solutions in decamethylcyclopentasiloxane or isododecane. Descriptions of the specific test methods and composition of the cosmetic formulation used in these evaluations follows Table 6.

TABLE 6

| Example # | 60° Gloss | Tack | Foundation Durability - ΔE (Change in color) | Curl Retention - Hair - % curl maintained after 5 hours at 95% RH | Hair Conditioning - Wet Comb % Reduction in combing force | Hair Conditioning - Dry Comb % Reduction in combing force |
|---|---|---|---|---|---|---|
| No Resin - neg control | 55 blank chart | | 9.2 | 30.5–36.8 | −95 (exposed to water only) | −50 (exposed to water only) |
| MQ resin | 34.8 | Not tacky | 3.8 | 53–58 | −55.7 | −1650 |
| T propyl resin | 78.4 | Very tacky | 11.0 | 44 | | |
| 1-a | 72.6 | Not Tacky | 5.1 | 45.5 | | |
| 1-b | 74.5 | slight, less w/time | 4.7 | 50.6 | −65 | −1648 |
| 1-c | 75.2 | slight, less w/time | 5.4 | 51.2 | 2.2 | −1508 |
| 1-d | 68.2 | Not tacky | | | | |
| 1-e | 68.7 | Not tacky | | | | |
| 2-a | 62.3 | Not Tacky | 3.1 | 41.3 | | |
| 2-b | 75.0 | Not Tacky | 4.0 | 33.2 | | |
| 2-c | 80.9 | Not Tacky | 6.9 | 33.9 | | |
| 3-a | 69.5 | Not tacky | 3.9 | | | |
| 3-b | 76.6 | Not Tacky | | 46.9 | −31.5 | −337 |

Gloss Measurement
1) Coat Leneta charts (Form N2C) with solution using a #8 Meyer rod
2) Allow chart to dry for 1 hour. Measure 60° gloss using a portable gloss meter at 3 points on the left ⅓ of the chart. Calculate the average of the 3 gloss values. Evaluate coating for tack, greasiness, fingerprint mark and if and how the coating rubs off the chart.
3) 4 hours after the drawdown was completed, measure 60° gloss using a portable gloss meter at 3 points on the middle ⅓ of the chart. Calculate the average of the 3 gloss values. Evaluate coating for tack, greasiness, fingerprint mark and if and how the coating rubs off the chart.
4) 24 hours after the drawdown was completed, measure 60° gloss using a portable gloss meter at 3 points on the right ⅓ of the chart. Calculate the average of the 3 gloss values. Evaluate coating for tack, greasiness, fingerprint mark and if and how the coating rubs off the chart.
5) Using the average gloss at the 3 different times, calculate the overall average.

Curl Retention Test Method
Materials
Prepared natural virgin brown hair tresses or oriental hair of 2 g, 25 cm.
Comb Trade Mark: Ace; reference 2618/6-GB.
Humidity chamber to regulate temperature and humidity during test.
Procedure for Pre-Treating the Swatches (Washing):
1) Wet 5 tresses for 30 sec with tap water at 37° C.
2) Lather the 5 tresses for 30 sec. With 5 g of the 30% SLS solution (Empicol LX28/Albright & Wilson), stroking the tresses downward, ensure you repeat the same movement for all the hair washed. Leave on hair for 30 sec.
3) Rinse the tresses for 1 minute with tap water at 37° C.
4) Remove the excess of water by running the tresses between the two fingers 3 times.
5) Allow the tresses to dry overnight on a paper towel at room temperature.
Procedure for Treating the Swatches with the Resin and Curling:
Blank or negative control is the solvent used in the treatments.
1) Dip 1 tress at a time 3 times in 37° C. tap water and remove excess of water by stroking the tress between 2 fingers
2) Lay the tress down on a clean support and apply 100 microliters of a 6% resins solution all along the using a calibrated micropipette
3) Detangle the tress completely
4) Roll the tress on rod spiral curler,
5) Leave the swatches to dry overnight in an oven at 40° C.
Test-Curl Retention Measurements:
1. Start the humidity chamber 2 hours before the test set at 70% humidity and 25 C.
2. Carefully remove the roller from hair by twisting it slightly, 10 minutes before the start of the test. Cut the ends of the tress in order to make it even (cut as few as possible).
3. Ensure each tress is correctly curled.
4. Hang the tresses in the humidity chamber: the bottom of the wax sealing on the tress should be on the line "0" of the millimeter paper sheet in the back of the chamber.
5. Measure hair tress length at predetermined intervals of time, the length is measured as the distance between the bottom of the wax sealing and the bottom of the tress—be aware that the bottom of the tress is going down, so the view angle is always be perpendicular to the glass.
6. After the 5 hours, remove the tresses from the humidity chamber and measure the tress length at its maximum, by unrolling it completely. Calculate curl retention as described below.
Percent curl retention is calculated as follows:

$$\% \text{ Curl Retention} = \frac{\text{max length} - \text{length at } T = x}{\text{max length} - \text{length at } T = 0} \times 100$$

Instron Test for Hair Conditioning for Dry or Wet Hair
Materials

Testing was performed on slightly bleached European.

Comb Trade Mark: Unbreakable or Ace Brand (Fine tooth spacing: 16 teeth/25 mm. Wide tooth spacing: 11 teeth/25 mm).

Hair Swatches Preparation and Baseline Testing:
1) Weigh out between 2.35 and 2.50 g. hair
2) Rough up lower half of plastic tab with sandpaper
3) Cut ~½" off root end of hair.
4) Put glue in middle of sanded end of tab and lay hair on the glue. Squeeze more glue on top of hair; then using another plastic tab press glue into hair while evenly spreading the hair and glue onto the tab keeping ~⅛ to ¼ inch away from sides.
5) Cut tress to 6"±0.25" from bottom of tab.
6) Let glue dry overnight.
7) Punch hole in middle of tab ~¼" from the top.
8) Wash all tresses according to the following procedure:
  a) Wet hair tress under 40 degree C. tap water for 15 seconds.
  b) Using a pipette, apply 1.0 g of 9% Sodium Lauryl Sulfate (active) and stroke through tress for 30 seconds.
  c) Rinse tress under the running water for 30 seconds.
  d) Place tresses on paper towel covered tray and dry overnight.
  e) Comb through tress three times with narrow teeth.
9) Measure force it takes to comb the untreated tresses before treatment using an Inston machine. Take force measurements on dry and wet hair as follows before treatment.

Ensure that the temperature and humidity inside the test room are appropriate for testing (approximately 70 deg F. and 30% RH).
  a) A 5 kilogram load cell is used for the testing
  b) Place 2 combs in the holders with wide-spaced teeth on the left and fine teeth on the right. Secure combs with holder screws so that approximately 1" of combs are sticking out of the front of the holder and over-lapping each other. For untreated tresses, use the same combs for combing all tresses; but for treated tresses, use different combs for every different treatment.
  c) Dry Combing Procedure: Detangle hair by combing tress 3 times, Retangle hair by swirling tress clockwise 3 times and counter clockwise 3 times, place tress on hanger and use Instron to comb through tresses.
  d) Wet Combing Procedure: Wet hair by dipping in distilled water and detangle hair by combing tress 3 times, retangle hair by dipping in distilled water three times, remove excess water by passing tress through index and middle fingers twice, place tress on hanger and use Instron to comb tress.

Procedure for Treating and Testing the Swatches with Resin Solution:
1) Wet the tresses for 15 sec under tap water at 40° C.
2) Remove the excess water by pulling tress through index and middle fingers.
3) Lay the tresses on a clean support and apply 100 microliters of 6% active silicone product using a calibrated micropipette.
4) Allow solution to dry on hair 60 minutes for ethanol-based solutions, overnight for aqueous to test on dry hair.
5) Comb through tresses once before performing Instron study on both dry and wet hair see 9 from previous section.

Foundation Formulation
Pigment Premix:
50 wt % DC 245 Fluid
13.16 wt % Carde AS Titanium dioxide (caprylyl silane treated)
11.41 wt % Carde AS Red Iron Oxide(caprylyl silane treated)
18.26 wt % Carde AS Yellow Iron Oxide(caprylyl silane treated)
7.17 wt % Carde AS Black Iron Oxide(caprylyl silane treated)
Procedure:
1) Place DC 245 fluid in Waring Blender
2) Add titanium dioxide and mix by pressing the pulse button for 2 seconds for 15 seconds total.
3) Add red iron oxide and mix the same as titanium dioxide
4) Continue with the other pigments
5) When all materials have been dispersed, mix on high and shred for 30 sec to grind the pigments
6) Place premix into a round glass jar and place on pail roller for 6 hours.

Phase A
20.50 wt % Pigment Premix
7.50 wt % DC 5225C
8 wt % of a 50% resin solids in solvent
Phase B
54.80 wt % DI Water
1.0 wt % NaCl
0.20 wt % Polysorbate 20
Procedure for Liquid Water in oil Foundation
1) Put pigment dispersion on roller for 1 hour.
2) Weigh out resin and solvent to make a 50% solids dilution. Use oven and wheel to mix
3) Combine ingredients in Phase A, mix until uniform using a dual blade, turbulent style mixing action.
4) Combine ingredients in Phase B in separate beaker, mix until uniform using a magnetic stirrer
5) Increase mixing speed of Phase A to 1376 rpm and very slowly add Phase B through an addition funnel. This addition should take 10 mins.

Continue mixing for an additional 10 min.

Foundation Durability Method: Gardner Abrasion Tester
1. Cut collagen into 3.5"×3" pieces, place one on each of the 3"×2.5" polycarbonate blocks and put in the humidity chamber overnight. This chamber must be at a constant 98% relative humidity level.
2. Remove collagen and block from chamber. Secure collagen to block with Scotch tape taking care not to place any tape on the top of the block's surface.
3. Add approximately 1 gram of foundation to the collagen, beading it across the top of the block. Using a #8 Meyer rod, coat the collagen with the foundation by placing the rod on the bead of foundation and spreading it downward to the bottom of the block. The final coating weight should be approximately 0.2 grams. This operation may need to be repeated to obtain the proper coating weight. Remove any material from the sides of the block.
4. Allow sample on collagen to dry. Drying times vary with different samples. Entire sample must be free from any wetness before testing. Measure color of sample on collagen for the initial baseline color using a spectrophotometer or colorimeter. L*, a*, and b* designate the place of the colored object in a tri-dimensional space.
5. Place block with collagen face-up on the Gardner Abrasion Tester making sure that the block is in the tester. The soft side of Velcro is attached to the insult block to abrade or insult the foundation sample on the collagen. The insult block rubs back and forth across the foundation sample. One insult consists of one back and forth motion. Insult the foundation sample on the collagen 20 times. The machine can be stopped at certain intervals to measure the color.

6. After the foundation sample is insulted 20 times, the color is read as L*, a*, b* and the change in color, ΔE, is calculated (see equation below). The number of insults, coating weight, and repetitions can be changed to fit the needs of the material being tested. This is up to the discretion of the operator.

$$\Delta L^*, \Delta a^* \text{ and } \Delta b^* = \text{value after abrasion} - \text{value at initial baseline before abrasion.}$$

$$\Delta E = (\Delta L^2 + \Delta a^{*2} + \Delta b^{*2})^{1/2}$$

With larger ΔE's, more foundation was removed and therefore the foundation is less durable.

The invention claimed is:

1. A siloxane resin comprising the units:
   (i) $(R^1_3SiO_{1/2})_a$
   (ii) $(R^2_2SiO_{2/2})_b$
   (iii) $(R^3SiO_{3/2})_c$, and
   (iv) $(SiO_{4/2})_d$
   wherein
   $R^1$, $R^2$, and $R^3$ are independently an alkyl group having from 1 to 8 carbon atoms, an aryl group, a carbinol group, or an amino group,
   a has a value 0.05 to 0.5,
   b has a value of zero to 0.3,
   c has a value of 0.05 to 0.65,
   d has a value of 0.05 to 0.6,
   the value of a+b+c+d=1,
   and the siloxane resin has a weight average molecular weight of 26,900 to 25,300,000 and with the proviso that greater than 40 mole % of the $R^3$ groups in the siloxane resin are propyl.

2. The siloxane resin of claim 1 wherein the siloxane resin is selected from MQ-T propyl resins comprising the units;
   $((CH_3)_3SiO_{1/2})_a$,
   $(R^3SiO_{3/2})_c$, where $R^3=CH_3CH_2CH_2-$, and
   $(SiO_{4/2})_d$
   MQ-T propyl resins comprising the units;
   $((CH_3)_3SiO_{1/2})_a$,
   $((CH_3)_2SiO_{2/2})_b$,
   $(R^3SiO_{3/2})_c$, where $R^3=CH_3CH_2CH_2-$, and
   $(SiO_{4/2})_d$
   MQ-T propyl resins comprising the units;
   $((CH_3)_3SiO_{1/2})_a$,
   $((CH_3)_2SiO_{2/2})_b$, $((CH_3)(C_6H_5)SiO_{2/2})_b$,
   $(R^3SiO_{3/2})_c$, where $R^3=CH_3CH_2CH_2-$, and
   $(SiO_{4/2})_d$
   MQ-T propyl resins comprising the units;
   $((CH_3)_3SiO_{1/2})_a$,
   $((CH_3)_2SiO_{2/2})_b$,
   $(R^3SiO_{3/2})_c$, where $R^3=CH_3CH_2CH_2-$, and $(C_6H_5SiO_{3/2})_c$
   $(SiO_{4/2})_d$
   MQ-T propyl resins comprising the units;
   $((CH_3)_3SiO_{1/2})_a$,
   $((CH_3)_2SiO_{2/2})_b$, $((CH_3)(C_6H_5)SiO_{2/2})_b$,
   $(R^3SiO_{3/2})_c$, where $R^3=CH_3CH_2CH_2-$, $(C_6H_5SiO_{3/2})_c$, and
   $(SiO_{4/2})_d$
   wherein a has a total value in the resin of 0.05 to 0.5, the sum of b+b' has a total value in the resin of zero to 0.3, c has a total value in the resin of 0.05 to 0.65, and d has a total value in the resin of 0.05 to 0.6.

3. A method of making a siloxane resin comprising reacting:
   A) a MQ resin comprising at least 80 mole % $(R^1_3SiO_{1/2})_a$ and $(SiO_{4,2})_d$ units
      where $R^1$ is an alkyl group having from 1 to 8 carbon atoms, an aryl group, a carbinol group, or an amino group,
      a and d has a value greater than zero, and
      the ratio of a/d is 0.5 to 1.5;
   and
   B) a T propyl resin comprising at least 80 mole % $R^3SiO_{3/2}$ units,
      where $R^3$ is an alkyl group having from 1 to 8 carbon atoms,
      an aryl group, a carbinol group, or an amino group,
      c has a value greater than zero,
      and with the provisio that at least 40 mole % of the $R^3$ groups are propyl,
      wherein the weight ratio of A/B is from 95:5 to 15:85.

4. A personal care product comprising the siloxane resin of claim 1.

5. The personal care product of claim 4, where the personal care product is a cosmetic product.

6. The personal care product of claim 4, where the personal care product is a hair care product.

7. A personal care product comprising the siloxane resin of claim 2.

8. The personal care product of claim 7, where the personal care product is a cosmetic product.

9. The personal care product of claim 7, where the personal care product is a hair care product.

* * * * *